(12) United States Patent
Weigel et al.

(10) Patent No.: US 6,706,475 B1
(45) Date of Patent: Mar. 16, 2004

(54) OLIGONUCLEOTIDE PROBES FOR DETECTING ENTEROBACTERIACEAE AND QUINOLONE-RESISTANT ENTEROBACTERIACEAE

(75) Inventors: Linda M. Weigel, Decatur, GA (US); Fred C. Tenover, Atlanta, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/647,563

(22) PCT Filed: Mar. 30, 1999

(86) PCT No.: PCT/US99/06963
§ 371 (c)(1),
(2), (4) Date: Jan. 16, 2001

(87) PCT Pub. No.: WO99/50458
PCT Pub. Date: Oct. 7, 1999

(51) Int. Cl.[7] .......................... C12Q 1/68; C12P 19/34; G01N 33/00; C07H 21/02; C07H 21/04
(52) U.S. Cl. .......................... 435/6; 435/91.1; 436/94; 536/23.1; 536/24.3; 536/24.33
(58) Field of Search .......................... 435/6, 7.2, 7.37, 435/91.1, 183; 436/94; 536/23.1, 23.2, 23.7, 24.3, 24.33, 25.3

(56) References Cited

U.S. PATENT DOCUMENTS 5,645,994 A   7/1997   Huang

FOREIGN PATENT DOCUMENTS

EP   0 688 873   1/1998

OTHER PUBLICATIONS

Bachoul et al., *Microbial Drug Resistance* (1998) 4:4, pp. 271–276.
Cambau et al., *Drugs* (1993) 45(Suppl. 3):15–23.
Deguchi et al., *Journal of Antimicrobial Chemotherapy* (1997) 40: pp. 543–549.
Deguchi et al., *Antimicrobial Agents and Chemotherapy* (1997) 41:11, pp. 2544–2546.
Dimri et al., *Nucleic Acids Research* (1990) 18:151–156.
Everett et al., *Antimicrob. Agents Chemother.* (1996) 40:2380–2386.
Guillemin et al., *Antimicrob. Agents Chemo.* (1995) 39(9):2145–2149.
Heisig et al., *Antimicrob. Agents Chemother.* (1993) 37:696–701.
Hooper, *Antimicrob. Agents Chemother.* (1992) 36:1151–1154.
Hooper, *Adv. Expmtl. Medicine and Biology* (1995) 390:49–57.
Husmann et al., *J. Clin. Microbiol.*(1997) 35(9):2398–2400.
Kim et al., *Antimicrobial Agents and Chemotherapy* (1998) 42:1, pp. 190–193.
Nishino et al., *Fems Microbiology Letters* (1997) 154:2, pp. 409–414.
Ozeki et al., *Journal of Clinical Microbiology* (1997) 34:9, pp. 2315–2319.
Piddock, *Drugs* (1995) 49(Suppl):29–35.
Swanberg et al., *J. Mol. Biol.* (1987) 197:729–736.
Tankovic et al., *Antimicrob. Agents Chemother.* (1996) 40:2505–2510.
Vila et al., *Antimicrob. Agents Chemother.* (1994) 38:2477–2479.
Weigel et al., *Antimicrobial Agents and Chemotherapy* (1998) 42:10, pp. 2661–2667.
Yoshida et al., *Antimicrob. Agents Chemother.* (1990) 34:1271–1272.

*Primary Examiner*—Ethan Whisenant
*Assistant Examiner*—Frank Wei Min Lu
(74) *Attorney, Agent, or Firm*—Klarquist Sparkman, LLP

(57) ABSTRACT

Oligonucleotide probes for detecting Enterobacteriaceae species. Unique gyrA coding regions permit the development of probes specific for eight different species: *Escherichia coli, Citrobacter freundii, Enterobacter aerogenes, Enterobacter cloacae, Klebsiella oxytoca, Klebsiella pneumoniae, Providencia stuartii*, and *Serratia marcescens*. The invention thereby provides methods for the species-specific identification of these Enterobacteriaceae in a sample, and detection and diagnosis of Enterobacteriaceae infection in a subject. Further, nucleic acids are provided for determining quinolone-resistant status of these Enterobacteriaceae.

15 Claims, 6 Drawing Sheets

```
EC-11775.DNA   25: ACACCGGTCAACATTGAGGAAGAGCTGAAGAGCTCCTATCTGGATTATGCGATGTCGGTC
CF-8090.DNA        ............................................................
EA-13048.DNA       ....G....................A....G.............................
ECL13047.DNA       ........T.....C..............................C..............
KO-13182.DNA       ............................................................
KP-13883.DNA       ..............T....A...T.....................................
PS-29914.DNA       ...........T..C..A.....A..C..A..T..G...T................C..T
SM-13880.DNA       ........A.....C..A..C...T....A.A...G........C............C..T
                   ****  ***  **  **  **  **  **    *  **  *    **  ***  ****  ***********   **

EC-11775.DNA   85: ATTGTTGGCCGTGCGCTGCCAGATGTCCGAGATGGCCTGAAGCCGGTACACCGTCGCGTA
CF-8090.DNA        ......................C...........................T.........
EA-13048.DNA       .....................G......................................
ECL13047.DNA       .....................G..C.....C..............................
KO-13182.DNA       .....................G.......................................
KP-13883.DNA       .....................G.......................................
PS-29914.DNA       .....C..G..C.....T........T.........A.........A........CA.A...
SM-13880.DNA       .....C..A.....C..........T..T.....A...........T.....C....T
                   *****  **  **  **  **  **  **  **  **  *****  ********  **  *****    *  **

EC-11775.DNA  145: CTTTACGCCATGAACGTACTAGGCAATGACTGGAACAAAGCCTATAAAAAATCTGCCCGT
CF-8090.DNA        .................T.G.....C........T..........................
EA-13048.DNA       ..A...............T.G...................................A......
ECL13047.DNA       ..A...............T.G.............T........C.................
KO-13182.DNA       ..A...............T.G.........................................
KP-13883.DNA       ..................T.G....................................A....
PS-29914.DNA       ..G.TT..G.....T...T.G..A.....T.....T...C......................
SM-13880.DNA       ..G.....G....G....T.G..T..C.......T...C.A..C..G.....G.......
                   **  *  **  ****  ***  *  **  **  **  *****  ***  *  **  **  *****  ******

EC-11775.DNA  205: GTCGTTGGTGACGTAATCGGTAAATACCATCCCCATGGTGACTCGGCGGTTTATGACACG
CF-8090.DNA        .......................C..T......TA.C..C.....C....C
EA-13048.DNA       ........C................C..G.....TA.C..C.........C
ECL13047.DNA       ...........................T..C.....G..C....C
KO-13182.DNA       .....G........C........C..T.......TA.T..C..A..C.....C
KP-13883.DNA       ...................C..G..C..C.....C.....A..C.....C
PS-29914.DNA       A.A..C..G.....T................A........TAGC..T........G..A
SM-13880.DNA       .....C..G.....G............T..C..G..C......AGC........C.....T
                   *  **  **  *****  ***********  **  **  **  **  **      **  **  **  **  **

EC-11775.DNA  265: ATCGTCCGTATGGCGCAGCCATTCTCGCTGCGTTACATGCTGGTAGACGGTCAGGGTAAC
CF-8090.DNA        ..T..T.....................CT........T...........
EA-13048.DNA       .....A...........G.....CT.......T........C..T..C.........
ECL13047.DNA       .....T.............T....................T..........
KO-13182.DNA       ..T..A................C.................T..C........
KP-13883.DNA       .....G..........G....................G.....C.........
PS-29914.DNA       .....T...C.T..T.....T..T..TA.......T.........T........G...
SM-13880.DNA       .....G........T.....G..T.A.....C.........G..............
                   **  **  ***  *  **  *****  **  **  ****  **  ********  **  **  *****  ***
```

Fig. 1A

```
EC-11775.DNA  325: TTCGGTTCCATCGACGGCGACTCTGCGGCGGCAATGCGTTATACGGAAATCCGTCTGGCG
CF-8090.DNA        ..T.....TG....T.........C..A.....G......................A..T..
EA-13048.DNA       ..T.....TG....T.........C..T..A..G......................A..T..
ECL13047.DNA       ..T.....T...............C..C...................................
KO-13182.DNA       ..T.....GG..............C..C..A..G......................A..T..
KP-13883.DNA       ..T.....................C..C.....G...............C....T........
PS-29914.DNA       ..T.....AG.T.....A..T..C..A..T...................A.....
SM-13880.DNA       ..........G...........C.........G...........C...G.G..CA..T.C
                   **  *****    *  **  **  **  **  **  *  **  ***********  ***  *  **    **  *

EC-11775.DNA  385: AAAATTGCCCATGAACTGATGGCTGATCTCGAAAAAGAGACGGTCGATTTCGTTGATAAC
CF-8090.DNA        .....C........G.........C..G........A.....T........C......
EA-13048.DNA       ..G..C..T.....G.........C...................T........C..C...
ECL13047.DNA       ..............G.........C..C..G............T...............
KO-13182.DNA       ..G..C..................C..C.......................G........C......
KP-13883.DNA       .....C..T.....G.........C.....T......................C..C...
PS-29914.DNA       ..............A..T.A..G.....T...........C..T........CCCA...
SM-13880.DNA       ..G.....T..C.....T....G.....G........A..C.....C.....GCC....
                   **  **  **  **  **    **  *  **  **  **  *******  **  **  **  *****      ***

EC-11775.DNA  445: TATGACGGTACGGAAAAAATTCCGGACGTCATGCCAACCAAAATTCCTAACCTGCTGGTG
CF-8090.DNA        ..C.....C..C.....C.......T..........G...........................
EA-13048.DNA       ........C.....G.....C..T..........G..A.....C..................
ECL13047.DNA       ..C..T..C............T............G..G..C.....................
KO-13182.DNA       ........C.....G.....C..T.....T.....G........C..G.......A..C
KP-13883.DNA       ..............GCGT..........G..................................
PS-29914.DNA       .....T.....A..GC....C..T..A..T.....T..G.....C..........AT....T
SM-13880.DNA       .....T..C..C..GC.G..C....C........G.....G..C..G..........C
                   **  **  **  **  **      **  **  *  **  *****  **  **  **  **  *****    *  **

EC-11775.DNA  505: AACGGTTCTTCCGGTATCGCCGTAGGTATGGCAACCAACATCCCGCCGCACAACCTGACG
CF-8090.DNA        ........G...........G..........G........T..................T
EA-13048.DNA       ............................G........T........T.........
ECL13047.DNA       ........G............G.....G.......T...........A.C..C
KO-13182.DNA       ........G............G........G..T..T..T...................C
KP-13883.DNA       .....CG.C.....G............G.....C......A.....A.T..........
PS-29914.DNA       ..T.....G..A.....T..T..T..G........G.....T..T..A........AGG.
SM-13880.DNA       .....C..G..G..C........G..C.....T.....T..T.................G..
                   **  **    *  **  **  **  **  **  **  **  *****  **  **  **  **  **  **  ***  *

EC-11775.DNA  565: GAAGTCATCAACGGTTGTCTGGCCGTATATCGATGATGAAGACATCAGCA
CF-8090.DNA        .....G........C........A.....T..C................
EA-13048.DNA       .....T........C..C.....A..CG.T...A.C..............
ECL13047.DNA       .....G........C..C.....C........C.................
KO-13182.DNA       .....G........C........C..CG.T..AA.C..............
KP-13883.DNA       .....G..T.....C.:.........G.T..C..................
PS-29914.DNA       .....G....G......C..T..T.....A..........T..T....
SM-13880.DNA       ......G.......C..C.....C......C.....A............
                   *****  *  *  ***  **  **  **  **  *  **  *  ***  *  **  ****
```

Fig. 1B

**DNA Sequence Similarity of the QRDR* in Enterobacteriaceae**

```
              199                                                        S83        258
E. coli**     GCCCGTGTCGTTGGTGACGTAAATCGGTAAATACCATCCCATGGTGACTCGGCGGTTTAT
C. freundii   ............................................C..T........TA.C.C....C
E. aerogenes  ...........................C.................C..G........TA.C.C....C
E. cloacae    ..........................................................T.C.....G..C
K. oxytoca    ...................G......C..................C..T........TA.T.C.A..C
K. pneumoniae .................................................C..G..C...C.....A..C
P. stuartii   ........A.A..C.G...T.........................T...A........TAGC.T.....
S. marcescens .......C..G....G..............T.C.G.C.........AGC.........
              ******  *  *  ****** *  *************** ** ** ****  ** *** ***

259                                                                   318
E. coli        GACACGATCGTCCGTATGGCGCAGCCATTCTCGCTGCGTTACATGCTGGTAGACGGTCAG
C. freundii   .....C..T..T....................CT.............T........
E. aerogenes  .....C...A...................G...CT............T.....C.T.C..
E. cloacae    .....C...T...................................T..........T......
K. oxytoca    .....C..T.A...............G..................C.........T.C....
K. pneumoniae .....C.......G................G.................G....C.
P. stuartii   .G.A....T..C.T.T.....T.T..TA.....T..........T.........
S. marcescens .....T...G...........T...G..T.A....C........**  ** ** *********  ***
              ** ** **** **  *** *  ***  ** ** ** ***** ** ** *********  ***
```

* Yoshida et al., 1990. Antimicrob. Agents Chemother. 34:1271.
 Swanberg and Wang, 1987. J. Mol. Biol. 197**:729.

FIG_2

Similarity of the Amino Acid Sequences of the QRDR
of Enterobacteriaceae

```
          67                    83   87                  106
          ARVVGDVIGKYHPHGDSAVYDTIVRMAQPFSLRYMLVDGQ
E. coli   .......................................
C. freundii  .............T.........................
E. aerogenes .............T.........................
E. cloacae   .......................................
K. oxytoca   .............T.........................
K. pneumoniae .......................................
P. stuartii  ..I..................E...L......M.......
S. marcescens .......................................
```

Fig_3

|  | MIC (µg/ml)[1] | | | Amino acid change[2] GyrA | | |
| Strain | CIP | OFLX | SPAR | 81 | 83 | 87 (codon) |
|---|---|---|---|---|---|---|
| *C. freundii* | | | | | | |
| ATCC 8090 | ≤0.12 | ≤0.25 | ≤0.008 | Gly(GGT) | Thr(ACC) | Asp(GAC) |
| Cf 7377 | 2 | 8 | >2 | – | Ile(ATC) | – |
| Cf 0759 | 2 | 8 | >2 | – | Ile(ATC) | – |
| Cf 9085 | 4 | 8 | 2 | – | Ile(ATC) | – |
| Cf 9417 | 8 | 8 | >2 | – | Ile(ATC) | – |
| Cf 1958 | ≥16 | ≥16 | >2 | – | Ile(ATC) | Gly(GGC) |
| Cf 5757 | ≥16 | ≥16 | >2 | – | Ile(ATC) | Gly(GGC) |
| Cf 9023 | ≥16 | ≥16 | >2 | – | Ile(ATC) | – |
| *E. aerogenes* | | | | | | |
| ATCC 13048 | 0.5 | 1 | 0.25 | Gly(GGT) | Thr(ACC) | Asp(GAC) |
| Ea 1747 | ≤0.12 | <0.25 | 0.06 | – | – | – |
| Ea 2786 | 2 | 4 | 2 | – | Ile(ATC) | – |
| Ea 9032 | 4 | 4 | 2 | – | Ile(ATC) | – |
| Ea 5593 | 8 | 8 | >2 | – | Ile(ATC) | – |
| Ea 9433 | 8 | ≥16 | >2 | – | Ile(ATC) | – |
| Ea 3521 | 8 | ≥16 | >2 | – | Ile(ATC) | – |
| Ea 5590 | 8 | ≥16 | >2 | – | Ile(ATC) | – |
| Ea 2775 | ≥16 | 32 | >2 | – | Ile(ATC) | – |
| *E. cloacae* | | | | | | |
| ATCC 13047 | ≤0.12 | ≤0.25 | 0.03 | Gly(GGT) | Ser(TCC) | Asp(GAC) |
| Ecl 1700 | ≤0.12 | <0.25 | 0.06 | – | – | – |
| Ecl 1524 | 0.25 | 0.5 | 0.12 | – | – | Asn(AAC) |
| Ecl 1963 | 2 | 4 | 2 | – | Phe(TTC) | – |
| Ecl 1286 | 2 | 4 | 1 | – | Tyr(TAC) | – |
| Ecl 3529 | 4 | 8 | >2 | – | Thr(ACC) | – |
| Ecl 1544 | 8 | 8 | >2 | – | Tyr(TAC) | – |
| Ecl 1627 | 8 | ≥16 | >2 | – | Tyr(TAC) | – |
| Ecl 9028 | ≥16 | 8 | >2 | – | Ile(ATC) | – |
| Ecl 1224 | ≥16 | 8 | >2 | – | Phe(TTC) | Asn(AAC) |
| Ecl 1251 | ≥16 | ≥16 | >2 | – | Ile(ATC) | – |
| Ecl 63 | ≥16 | ≥16 | >2 | – | Phe(TTC) | – |
| Ecl 105 | ≥16 | ≥16 | >2 | – | Phe(TTC) | – |
| Ecl 1783 | ≥16 | ≥16 | >2 | – | Tyr(TAC) | – |
| Ecl 9030 | ≥16 | ≥16 | >2 | – | Tyr(TAC) | – |
| Ecl 9031 | ≥16 | >32 | >2 | – | Ile(ATC) | – |
| *E. coli* | | | | | | |
| ATCC 11775 | ≤0.12 | ≤0.25 | 0.03 | Gly(GGT) | Ser(TCG) | Asp(GAC) |
| Ec 748 | ≤0.12 | ≤0.25 | 0.03 | – | – | – |
| Ec 3535 | 1 | 2 | 2 | – | Leu(TTG) | – |
| Ec 5524 | 2 | 8 | 2 | – | Leu(TTG) | – |
| Ec 9419 | ≥16 | 32 | >2 | – | Leu(TTG) | Gly(GGA) |
| Ec 9421 | ≥16 | 32 | >2 | – | Leu(TTG) | Tyr(TAC) |
| Ec 9425 | ≥16 | >32 | >2 | – | Leu(TTG) | Asn(AAC) |

Fig. 4A

|  | MIC (μg/ml) | | | Amino acid change | | |
|---|---|---|---|---|---|---|
|  |  |  |  |  | GyrA |  |
| Strain | CIP | OFLX | SPAR | 81 | 83 | 87 (codon) |
| *K. pneumoniae* | | | | | | |
| ATCC 13883 | 0.5 | ≤0.25 | 0.06 | Gly(GGC) | Ser(TCC) | Asp(GAC) |
| Kp 570 | ≤0.12 | ≤0.25 | 0.06 | - | - | - |
| Kp 1961 | ≤0.12 | ≤0.25 | 0.03 | - | - | - |
| Kp 2778 | ≤0.12 | ≤0.25 | 0.03 | - | - | - |
| Kp 2790 | ≤0.12 | ≤0.25 | 0.03 | - | - | - |
| Kp 1361 | 1 | 2 | 0.5 | - | Phe(TTC) | - |
| Kp 1362 | 1 | 2 | 1 | - | Phe(TTC) | - |
| Kp 1177 | 4 | ≥16 | >2 | - | Phe(TTC) | - |
| Kp 682 | ≥16 | ≥16 | >2 | - | Phe(TTC) | - |
| Kp 1768 | ≥16 | 32 | >2 | - | Tyr(TAC) | - |
| Kp 1775 | ≥16 | >32 | >2 | - | Phe(TTC) | Gly(GGC) |
| Kp 1565 | ≥16 | >32 | >2 | - | Tyr(TAC) | Asn(AAC) |
| *K. oxytoca* | | | | | | |
| ATCC 13182 | ≤0.12 | ≤0.25 | 0.12 | Gly(GGT) | Thr(ACT) | Asp(GAC) |
| Ko 702 | ≤0.12 | ≤0.25 | 0.03 | - | - | - |
| Ko 2538 | ≤0.12 | ≤0.25 | 0.06 | - | - | - |
| Ko 2110 | ≤0.12 | ≤0.25 | 0.06 | - | - | - |
| Ko 1199 | ≤0.12 | ≤0.25 | 0.06 | - | - | - |
| Ko 57 | 0.5 | 0.05 | 0.25 | - | Ile(ATT) | - |
| Ko 1577 | 4 | 4 | 2 | - | Ile(ATT) | - |
| Ko 1817 | 8 | ≥16 | >2 | - | Ile(ATT) | - |
| Ko 466 | ≥16 | 8 | >2 | - | Ile(ATT) | - |
| Ko 32 | ≥16 | ≥16 | >2 | - | Ile(ATT) | - |
| Ko 1578 | ≥16 | ≥16 | >2 | - | Ile(ATT) | - |
| Ko 1612 | ≥16 | ≥16 | >2 | - | Ile(ATT) | - |
| Ko 2777 | ≥16 | >32 | >2 | - | Ile(ATT) | - |
| *P. stuartii* | | | | | | |
| ATCC 29914 | ≤0.12 | ≤0.25 | ≤0.12 | Gly(GGT) | Ser(AGC) | Glu(GAG) |
| Ps 1571 | 0.25 | 1 | 0.5 | - | - | - |
| Ps 1284 | 2 | 4 | 2 | - | Arg(CGC) | - |
| Ps 2469 | 8 | ≥16 | >2 | - | Ile(ATC) | - |
| Ps 2783 | ≥16 | ≥16 | 2 | - | Arg(AGG) | - |
| Ps 9428 | ≥16 | ≥16 | >2 | - | Ile(ATC) | - |
| Ps 7375 | ≥16 | 32 | >2 | - | Ile(ATC) | - |
| Ps 2468 | ≥16 | 32 | >2 | - | Ile(ATC) | - |
| Ps 1773 | ≥16 | >32 | >2 | - | Arg(AGG) | - |
| *S. marcescens* | | | | | | |
| ATCC 13880 | 0.5 | 1 | 1 | Gly(GGT) | Ser(AGC) | Asp(GAC) |
| Sm 1714 | 0.25 | 1 | 1 | - | Ile(ATC) | - |
| Sm 9745 | 2 | 4 | 2 | - | - | - |
| Sm 1221 | 4 | 8 | >2 | Cys(TGT) | - | - |
| Sm 1969 | 4 | ≥16 | >2 | - | - | Asn(AAC) |
| Sm 1570 | 8 | 8 | >2 | Cys(TGT) | - | - |
| Sm 5591 | 8 | ≥16 | >2 | - | Arg(AGA) | - |
| Sm 1568 | ≥16 | ≥16 | >2 | - | Arg(CGC) | - |

[1] CIP, ciprofloxacin; OFLX, ofloxacin; SPAR, sparfloxacin
[2] -, identical to the ATCC type strain

Fig. 4B

SEQUENCE LISTING

<160> NUMBER OF SEQ ID NOS: 35

<210> SEQ ID NO 1
<211> LENGTH: 589
<212> TYPE: DNA
<213> ORGANISM: Escherichia coli

<400> SEQUENCE: 1
acaccggtca acattgagga agagctgaag agctcctatc tggattatgc gatgtcggtc     60
attgttggcc gtgcgctgcc agatgtccga gatggcctga agccggtaca ccgtcgcgta    120

```
ctttacgcca tgaacgtact aggcaatgac tggaacaaag cctataaaaa atctgcccgt    180
gtcgttggtg acgtaatcgg taaataccat ccccatggtg actcggcggt ttatgacacg    240
atcgtccgta tggcgcagcc attctcgctg cgttacatgc tggtagacgg tcagggtaac    300
ttcggttcca tcgacggcga ctctgcggcg gcaatgcgtt atacggaaat ccgtctggcg    360
aaaattgccc atgaactgat ggctgatctc gaaaaagaga cggtcgattt cgttgataac    420
tatgacggta cggaaaaaat tccggacgtc atgccaacca aaattcctaa cctgctggtg    480
aacggttctt ccggtatcgc cgtaggtatg caaccaaca tcccgccgca caacctgacg     540
gaagtcatca acggttgtct ggcgtatatc gatgatgaag acatcagca                589

<210> SEQ ID NO 2
<211> LENGTH: 589
<212> TYPE: DNA
<213> ORGANISM: Citrobacter freundii

<400> SEQUENCE: 2
acaccggtca acattgagga agagctgaag agctcctatc tggattatgc gatgtcggtc      60
attgttggcc gtgcgctgcc agacgtccga gatggcctga agccggttca ccgtcgcgta     120
ctttacgcca tgaacgtatt gggcaacgac tggaataaag cctataaaaa atctgcccgt     180
gtcgttggtg acgtaatcgg taaataccac cctcatggtg ataccgccgt ttacgacacc     240
attgttcgta tggcgcagcc attctccttg cgttacatgc tggtagatgg tcagggtaac     300
tttggttctg tcgatggcga ctccgcagcg gcgatgcgtt atacggaaat ccgtatgtcg     360
aaaatcgccc atgagctgat ggctgacctg gaaaaagaaa cggttgattt cgtcgataac     420
tacgacggca ccgaacaaat tcctgacgtc atgccgacca aaattcctaa cctgctggtg     480
aacggttcgt ccggtatcgc ggtaggtatg gcgaccaaca ttccgccgca caacctgact     540
gaagtgatca acggctgtct ggcatatatt gacgatgaag acatcagca                589

<210> SEQ ID NO 3
<211> LENGTH: 589
<212> TYPE: DNA
<213> ORGANISM: Enterbacter aerogenes

<400> SEQUENCE: 3
acacgggtca acattgagga agagctgaaa agctcgtatc tggattatgc gatgtcggtc      60
attgttggcc gtgcgctgcc ggatgtccga gatggcctga agccggtaca ccgtcgcgta     120
ctatacgcca tgaacgtatt gggcaatgac tggaacaaag cctataaaaa atcagcccgt     180
gtcgttggcg acgtaatcgg taaataccac ccgcatggtg ataccgccgt ttatgacacc     240
atcgtacgta tggcgcagcc gttctccttg cgttatatgc tggtcgatgg ccagggtaac     300
tttggttctg tcgatggcga ctccgctgca gcgatgcgtt atacggaaat ccgtatgtcg     360
aagatcgctc atgagctgat ggccgatctc gaaaaagaga cggttgattt cgtcgacaac     420
tatgacggca cggagaaaat ccctgacgtc atgccgacaa aaatcctaa cctgctggtg      480 aacggttctt ccggtatcgc cgtaggtatg gcgaccaaca ttccgccgca taacctgacg     540
gaagttatca acggctgcct ggcatacgtt gataacgaag acatcagca                589

<210> SEQ ID NO 4
<211> LENGTH: 589
<212> TYPE: DNA
<213> ORGANISM: Enterobacter cloacae

<400> SEQUENCE: 4
```

-continued

```
acaccggtta acatcgagga agagctgaag agctcctatc tggactatgc gatgtcggtc    60
attgttggcc gtgcgctgcc ggacgtccgc gatggcctga agccggtaca ccgtcgcgta   120
ctatacgcca tgaacgtatt gggcaatgac tggaataaag cctacaaaaa atctgcccgt   180
gtcgttggtg acgtaatcgg taaataccat cccatggtg attccgcggt gtacgacacc    240
atcgttcgta tggcgcagcc tttctcgctg cgttacatgc tggtagatgg tcagggtaac   300
tttggttcta tcgacggcga ctccgccgcg gcaatgcgtt atacggaaat ccgtctggcg   360
aaaattgccc atgagctgat ggccgacctg aaaaagaga cggttgattt cgttgataac    420
tacgatggca cggaaaaaat tcctgacgtc atgccaacga agatccctaa cctgctggtg   480
aacggttcgt ccggtatcgc cgtagggatg gcgaccaaca ttccgccgca caacatcacc   540
gaagtgatca acggctgcct ggcctatatc gacgatgaag acatcagca             589
```

<210> SEQ ID NO 5
<211> LENGTH: 589
<212> TYPE: DNA
<213> ORGANISM: Klebsiella oxytoca

<400> SEQUENCE: 5

```
acaccggtca acattgagga agagctgaag agctcctatc tggattatgc gatgtcggtc    60
attgttggcc gtgcgctgcc ggatgtccga gatggcctga agccggtaca ccgtcgcgta   120
ctatacgcca tgaacgtatt gggcaatgac tggaacaaag cctataaaaa atctgcccgt   180
gtcgtgggtg acgtcatcgg taaataccac cctcatggtg atactgccgt atacgacacc   240
attgtacgta tggcgcagcc attctccctg cgttacatgc tggtagatgg ccagggtaac   300
tttggttcgg tcgacggcga ctccgccgca gcgatgcgtt atacggaaat ccgtatgtcg   360
aagatcgccc atgaactgat ggccgacctc gaaaaagaga cggtggattt cgtcgataac   420
tatgacggca cggagaaaat ccctgacgtt atgccgacca aaatcccgaa cctgctagtc   480
aacggttcgt ccggtatcgc ggtaggtatg cgactaata ttccgccgca caacctgacc    540
gaagtgatca acggctgtct ggcctacgtt gaaaacgaag acatcagca             589
```

<210> SEQ ID NO 6
<211> LENGTH: 589
<212> TYPE: DNA
<213> ORGANISM: Klebsiella pneumoniae

<400> SEQUENCE: 6

```
acaccggtca acattgagga agagcttaag aactcttatc tggattatgc gatgtcggtc    60
attgttggcc gtgcgctgcc ggatgtccga gatggcctga agccggtaca ccgtcgcgta   120
ctttacgcca tgaacgtatt gggcaatgac tggaacaaag cctataaaaa atcagcccgt   180
gtcgttggtg acgtaatcgg taaataccac ccgcacggcg actccgcggt atacgacacc   240
atcgtgcgta tggcgcagcc gttctcgctg cgttacatgc tggtggacgg ccagggtaac   300
tttggttcca tcgacggcga ctccgccgcg gcgatgcgtt ataccgaaat tcgtctggcg   360
aaaatcgctc atgagctgat ggccgatctt gaaaaagaga cggtcgattt cgtcgacaac   420
tatgacggta cggagcgtat tccggacgtc atgccgacca aaattcctaa cctgctggtg   480
aacggcgcct ccgggatcgc cgtagggatg gccaccaaca taccgccaca taacctgacg   540
gaagtgatta acggctgtct ggcgtatgtt gacgatgaag acatcagca             589
```

<210> SEQ ID NO 7

```
<211> LENGTH: 589
<212> TYPE: DNA
<213> ORGANISM: Providencia stuartii

<400> SEQUENCE: 7
acaccggtca atatcgaaga agaactcaaa agttcgtatt tggattatgc gatgtccgtt      60
attgtcgggc gcgcgcttcc agatgttcga gatggactga agccagtaca ccgcagagta    120
ctgtttgcga tgaatgtatt gggaaatgat tggaataaac cctataaaaa atctgcccgt    180
atagtcgggg acgttatcgg taaataccat ccacatggtg atagcgctgt ttatgagaca    240
atcgttcgtc ttgctcagcc tttttctatg cgttatatgc tggtagatgg tcaggggaac    300
tttggttcag ttgacggaga ttccgcagct gcaatgcgtt atacgaaat ccgtatggcg      360
aaaattgccc atgaaatgtt agcggatctt gaaaagaga ccgttgattt cgtcccaaac      420
tatgatggta cagagcaaat ccctgaagtt atgcctacga aaatccctaa cctattggtt    480
aatggttcgt caggtattgc tgttgggatg caacgaaca ttcctccaca caacctaggg      540
gaagtgatca gcggttgcct tgcttatata gatgatgaag atattagca                589

<210> SEQ ID NO 8
<211> LENGTH: 589
<212> TYPE: DNA
<213> ORGANISM: Serratia marcescens

<400> SEQUENCE: 8
acaccggtaa acatcgaaga cgagttgaaa aactcgtatc tggactatgc gatgtccgtt      60
attgtcggac gtgccctgcc agatgttcgt gatggactga agccggttca ccgccgcgtt    120
ctgtacgcga tgagcgtatt gggtaacgac tggaataaac catacaagaa atcggcccgt    180
gtcgtcgggg acgtgatcgg taaatatcac ccgcacggtg acagcgcggt ttacgacact    240
atcgtgcgta tggctcagcc gttttcactg cgctacatgc tggtggacgg tcagggtaac    300
ttcggttccg tcgacggcga ctccgcggcg gcgatgcgtt ataccgaagt gcgcatgtcc    360
aagattgctc acgaactgtt ggcggatctg gaaaaagaaa ccgtcgactt cgtgcctaac    420
tatgatggca ccgagcagat cccggccgtc atgccgacca agatcccgaa cctgctggtc    480
aacggctcgt cgggcatcgc cgtgggcatg gctaccaata ttccgccgca caacctggcg    540
gaagtcgtca acggctgcct ggcctatatc gacgatgaaa acatcagca                589

<210> SEQ ID NO 9
<211> LENGTH: 120
<212> TYPE: DNA
<213> ORGANISM: Escherichia coli

<400> SEQUENCE: 9
gcccgtgtcg ttggtgacgt aatcggtaaa taccatcccc atggtgactc ggcggtttat      60
gacacgatcg tccgtatggc gcagccattc tcgctgcgtt acatgctggt agacggtcag    120

<210> SEQ ID NO 10
<211> LENGTH: 120
<212> TYPE: DNA
<213> ORGANISM: Citrobacter freundii

<400> SEQUENCE: 10
gcccgtgtcg ttggtgacgt aatcggtaaa taccaccctc atggtgatac cgccgtttac      60
gacaccattg ttcgtatggc gcagccattc tccttgcgtt acatgctggt agatggtcag    120
```

<210> SEQ ID NO 11
<211> LENGTH: 120
<212> TYPE: DNA
<213> ORGANISM: Enterobacter aerogenes

<400> SEQUENCE: 11
gcccgtgtcg ttggcgacgt aatcggtaaa taccacccgc atggtgatac cgccgtttat    60
gacaccatcg tacgtatggc gcagccgttc tccttgcgtt atatgctggt cgatggccag   120

<210> SEQ ID NO 12
<211> LENGTH: 120
<212> TYPE: DNA
<213> ORGANISM: Enterobacter cloacae

<400> SEQUENCE: 12
gcccgtgtcg ttggtgacgt aatcggtaaa taccatcccc atggtgattc cgcggtgtac    60
gacaccatcg ttcgtatggc gcagcctttc tcgctgcgtt acatgctggt agatggtcag   120

<210> SEQ ID NO 13
<211> LENGTH: 120
<212> TYPE: DNA
<213> ORGANISM: Klebsiella oxytoca

<400> SEQUENCE: 13
gcccgtgtcg tgggtgacgt catcggtaaa taccacccctc atggtgatac tgccgtatac    60
gacaccattg tacgtatggc gcagccattc tccctgcgtt acatgctggt agatggccag   120

<210> SEQ ID NO 14
<211> LENGTH: 120
<212> TYPE: DNA
<213> ORGANISM: Klebsiella pneumoniae

<400> SEQUENCE: 14
gcccgtgtcg ttggtgacgt aatcggtaaa taccacccgc acggcgactc cgcggtatac    60
gacaccatcg tgcgtatggc gcagccgttc tcgctgcgtt acatgctggt ggacggccag   120

<210> SEQ ID NO 15
<211> LENGTH: 120
<212> TYPE: DNA
<213> ORGANISM: Providencia stuartii

<400> SEQUENCE: 15
gcccgtatag tcggggacgt tatcggtaaa taccatccac atggtgatag cgctgtttat    60
gagacaatcg ttcgtcttgc tcagccttttt tctatgcgtt atatgctggt agatggtcag   120

<210> SEQ ID NO 16
<211> LENGTH: 120
<212> TYPE: DNA
<213> ORGANISM: Serratia marcescens

<400> SEQUENCE: 16
gcccgtgtcg tcggggacgt gatcggtaaa tatcacccgc acggtgacag cgcggtttac    60
gacactatcg tgcgtatggc tcagccgttt tcactgcgct acatgctggt ggacggtcag   120

<210> SEQ ID NO 17
<211> LENGTH: 25
<212> TYPE: DNA
<213> ORGANISM: Escherichia coli

<400> SEQUENCE: 17

```
actttacgcc atgaacgtac taggc                                    25

<210> SEQ ID NO 18
<211> LENGTH: 23
<212> TYPE: DNA
<213> ORGANISM: Citrobacter freundii

<400> SEQUENCE: 18
tgggcaacga ctggaataaa gcc                                      23

<210> SEQ ID NO 19
<211> LENGTH: 22
<212> TYPE: DNA
<213> ORGANISM: Enterobacter aerogenes

<400> SEQUENCE: 19
ttatatgctg gtcgatggcc ag                                       22

<210> SEQ ID NO 20
<211> LENGTH: 21
<212> TYPE: DNA
<213> ORGANISM: Enterobacter cloacae

<400> SEQUENCE: 20
gccggacgtc cgcgatggcc t                                        21

<210> SEQ ID NO 21
<211> LENGTH: 30
<212> TYPE: DNA
<213> ORGANISM: Klebsiella oxytoca

<400> SEQUENCE: 21
gtagatggcc agggtaactt tggttcggtc                               30

<210> SEQ ID NO 22
<211> LENGTH: 27
<212> TYPE: DNA
<213> ORGANISM: Klebsiella pneumoniae

<400> SEQUENCE: 22
gtgcgtatgg cgcagccgtt ctcgctg                                  27

<210> SEQ ID NO 23
<211> LENGTH: 25
<212> TYPE: DNA
<213> ORGANISM: Providencia stuartii

<400> SEQUENCE: 23
cgtcttgctc agccttttc tatgc                                     25

<210> SEQ ID NO 24
<211> LENGTH: 20
<212> TYPE: DNA
<213> ORGANISM: Serratia marcescens

<400> SEQUENCE: 24
ggaataaacc atacaagaaa                                          20

<210> SEQ ID NO 25
<211> LENGTH: 25
<212> TYPE: DNA
<213> ORGANISM: Escherichia coli

<400> SEQUENCE: 25
```

```
atggtgactc ggcggtttat gacac                                    25
```

<210> SEQ ID NO 26
<211> LENGTH: 25
<212> TYPE: DNA
<213> ORGANISM: Escherichia coli

<400> SEQUENCE: 26

```
atggtgactc ggcggtctat gacac                                    25
```

<210> SEQ ID NO 27
<211> LENGTH: 25
<212> TYPE: DNA
<213> ORGANISM: Citrobacter freundii

<400> SEQUENCE: 27

```
atggtgatac cgccgtttac gacac                                    25
```

<210> SEQ ID NO 28
<211> LENGTH: 25
<212> TYPE: DNA
<213> ORGANISM: Enterobacter aerogenes

<400> SEQUENCE: 28

```
atggtgatac cgccgtttat gacac                                    25
```

<210> SEQ ID NO 29
<211> LENGTH: 25
<212> TYPE: DNA
<213> ORGANISM: Enterobacter cloacae

<400> SEQUENCE: 29

```
atggtgattc cgcggtgtac gacac                                    25
```

<210> SEQ ID NO 30
<211> LENGTH: 25
<212> TYPE: DNA
<213> ORGANISM: Klebsiella oxytoca

<400> SEQUENCE: 30

```
atggtgatac tgccgtatac gacac                                    25
```

<210> SEQ ID NO 31
<211> LENGTH: 25
<212> TYPE: DNA
<213> ORGANISM: Klebsiella pneumoniae

<400> SEQUENCE: 31

```
acggcgactc cgcggtatac gacac                                    25
```

<210> SEQ ID NO 32
<211> LENGTH: 25
<212> TYPE: DNA
<213> ORGANISM: Providencia stuartii

<400> SEQUENCE: 32

```
atggtgatag cgctgtttat gagac                                    25
```

<210> SEQ ID NO 33
<211> LENGTH: 25
<212> TYPE: DNA
<213> ORGANISM: Serratia marcescens -continued

```
<400> SEQUENCE: 33
acggtgacag cgcggtttac gacac                                      25

<210> SEQ ID NO 34
<211> LENGTH: 18
<212> TYPE: DNA
<213> ORGANISM: Enterobacter sp.

<400> SEQUENCE: 34
cgaccttgcg agagaaat                                              18

<210> SEQ ID NO 35
<211> LENGTH: 18
<212> TYPE: DNA
<213> ORGANISM: Enterobacter sp.

<400> SEQUENCE: 35
gttccatcag cccttcaa                                              18
```

OLIGONUCLEOTIDE PROBES FOR DETECTING ENTEROBACTERIACEAE AND QUINOLONE-RESISTANT ENTEROBACTERIACEAE

This invention was made in the Centers for Disease Control and Prevention, an agency of the United States Government. The U.S. Govermnent has certain rights in this invention.

TECHNICAL FIELD OF THE INVENTION

This invention relates in general to the field of diagnostic microbiology. In particular, the invention relates to the species-specific detection of Enterobactedaceae.

BACKGROUND OF THE INVENTION

Enterobacteriaceae is a family of closely related, Gram-negative organisms associated with gastrointestinal diseases and a wide range of opportunistic infections. They are leading causes of bacteremia and urinary tract infections and are associated with wound infections, pneumonia, meningitis, and various gastrointestinal disorders. (Farmer, J. J., III. Enterobacteriaceae: Introduction and Identification in Murray, P. R., et al., *Manual of Clinical Microbiology*, Washington, D.C., ASM Press, 6th (32): 438–449 (1998)). Many of these infections are life threatening and are often nosocomial (hospital-acquired) infections. (Schaberg et al., *The Am. J. Med.*, 91:72s-75s (1991) and CDC NNIS System Report *Am. J. Infect. Control.*, 24:380–388 (1996)).

Conventional methods for isolation and identification of these organisms include growth on selective and/or differential media followed by biochemical tests of the isolated organism. Total incubation times require 24–48 hours. Slow-growing or fastidious strains require-extended incubation times. An additional 18–24 hours is required for susceptibility testing, usually by disk diffusion or broth dilution. More recently, the identification of bacteria by direct hybridization of probes to bacterial genes or by detection of amplified genes has proven to be more time efficient.

Quinolones are broad-spectrum antibacterial agents effective in the treatment of a wide range of infections, particularly those caused by Gram-negative pathogens. (Stein, *Clin. Infect. Diseases*, 23(Suppl 1):S19–24 (1996) and Maxwell, *J. Antimicrob. Chemother.*, 30:409–416 (1992)). For example, nalidixic acid is a first-generation quinolone. Ciprofloxacin is an example of a second generation quinolone, which is also a fluoroquinolone. Sparfloxacin is an example of a third generation quinolone, which is also a fluoroquinolone. As used herein, the term "quinolone" is intended to include this entire spectrum of antibacterial agents, including the fluoroquinolones. This class of antibiotics has many advantages, including oral administration with therapeutic levels attained in most tissues and body fluids, and few drawbacks. As a result, indiscriminate use has led to the currently increasing incidence of quinolone/fluoroquinolone resistance. Hooper, *Adv. Expmtl. Medicine and Biology*, 390:49–57 (1995). Mechanisms of resistance to quinolones include alterations in DNA gyrase and/or topoisomerase IV and decreased intracellular accumulation of the antibiotic due to alterations in membrane proteins. (Hooper et al., *Antimicrob. Agents Chemother.*, 36:1151–1154 (1992)).

The primary target of quinolones, including the fluoroquinolones, in Gram-negative bacteria is DNA gyrase, a type II topoisomerase required for DNA replication and transcription. (Cambau et al., *Drugs*, 45(Suppl. 3):15–23 (1993) and Deguchi et al., *J. Antimicrob. Chemother.*, 40:543–549 (1997)). DNA gyrase, composed of two A subunits and two B subunits, is encoded by the gyrA and gyrB genes. Resistance to quinolones has been shown to be associated most frequently with alterations in gyrA. (Yoshida et al., *Antimicrob. Agents Chemother.* 34:1271–1272 (1990)). These mutations are localized at the 5' end of the gene (nucleotides 199–318 in the *E. coli* gene sequence) in an area designated as the quinolone resistance-determining region, or QRDR, located near the active site of the enzyme, Tyr-122. (Hooper, *Adv. Expmtl. Medicine and Biology*, 390:49–57 (1995)).

Previous studies of fluoroquinolone-resistant strains of *Escherichia coli, Citrobacter freundii, Serratia marcescens* and *Enterobacter cloacae* have revealed that codons 81, 83, and 87 of gyrA are the sites most frequently mutated in Gram-negative organisms. (Nishino et al., *FEMS Microbiology Letters*, 154:409–414 (1997), and Kim et al., *Antimicrob. Agents Chemother.*, 42:190–193 (1998)). However, the association of gyrA mutations with fluoroquinolone resistance in *Enterobacter aerogenes, Klebsiella oxytoca*, and *Providencia stuartii* has not been established.

Previous publications have referred to the use of gyrA sequences to identify species within a single genus, such as Husmann et al.,*J. Clin. Microbiol.*, 35(9):2398–2400 (1997) for Campylobacters, and Guillemin et al., *Antimicrob. Agents Chemo.*, 39(9):2145–2149 (1995) for Mycobacterium. The complete gene sequences of DNA gyrase A has previously been published for *Escherichia coli* (Swanberg, et al., *J. Mol. Biol.*, 197:729–736 (1987)) and *Serratia marcescens* (Kim et al., *Antimicrob. Agents Chemother.*, 42:190–193 (1998)). Fragments of gyrA including the QRDR have been published for *Enterobacter cloacae* (Deguchi, *J. Antimicrob. Chemother.* 40:543–549 (1997)) and *Citobacter freundii* (Nishino et al., *FEMS Microbiology Letters*, 154:409–414 (1997)). Additionally, the putative gyrA sequence for *Klebsiella pneumoniae* was published (Dimri et al., *Nucleic Acids Research*, 18:151–156 (1990)), however, the present invention demonstrates that the most likely organism used in that work was *Klebsiella oxytoca*.

The prior art has not provided enough information about different Enterobacteriaceae to develop probes capable of distinguishing between as many species as desirable, nor for determining the quinolone resistance-status of the species. It would be desirable to characterize additional gyrA genes and mutations from quinolone-resistant Enterobacteriaceae for species-specific identification and quinolone resistance determination using oligonucleotide probes.

SUMMARY OF THE INVENTION

The present invention relates to oligonucleotide probes for detecting Enterobacteriaceae species. Unique gyrA coding regions permit the development of probes specific for identifying eight different species: *Escherichia coli, Citrobacter freundii, Enterobacter aerogenes, Enterobacter cloacae, Klebsiella oxytoca, Klebsiella pneumoniae, Providencia stuartii* and *Serratia marcescens*. The invention thereby provides methods for the species-specific identification of these Enterobacieriaceae in a sample, and detection and diagnosis of Enterobacteriaceae infection in a subject.

Furthermore, the described unique DNA sequences from the 5' end of gyrA, within or flanking the quinolone resistance-determining region, permit the development of probes specific for determining the quinolone-resistant status of eight different species: *Escherichia coli, Citrobacter freundii, Enterobacter aerogenes, Enterobacter cloacae,*

*Klebsiella oxytoca, Klebsiella pneumoniae, Providencia stuartii* and *Serratia marcescens*. The invention thereby provides methods for the species-specific identification of these quinolone-resistant Enterobacteriaceae, and detection and diagnosis of quinolone-resistant Enterobacteriaceae infection in a subject.

Therefore, it is an object of the invention to provide improved materials and methods for detecting and differentiating Enterobacteriaceae species and/or quinolone resistance in the clinical laboratory and -research settings.

These and other objects, features and advantages of the present invention will become apparent after a review of the following detailed description of the disclosed embodiments and the appended claims.

BRIEF DESCRIPTION OF THE DRAWINGS

FIGS. 1A and 1B show the nucleic acid sequence alignments for a portion of the gyrA gene in *Escherichia coli* (EC) (SEQ ID NO: 1), *Citrobacter freundii* (CF) (SEQ ID NO: 2), *Enterobacter aerogenes* (EA) (SEQ ID NO: 3), *Enterobacter cloacae* (ECL) (SEQ ID NO: 4), *Klebsiella oxytoca* (KO) (SEQ ID NO: 5), *Klebsiella pneumoniae* (KP) (SEQ ID NO: 6), *Providencia stuartii* (PS) (SEQ ID NO: 7), and *Serratia marcescens* (SM) (SEQ ID NO: 8).

FIG. 2 shows the DNA sequence similarity of the quinolone resistance-determining region (QRDR) in *Escherichia coli* (SEQ ID NO: 9), *Citrobacter freundii* (SEQ ID NO: 10), *Enterobacter aerogenes* (SEQ ID NO: 11), *Enterobacter cloacae* (SEQ ID NO: 12), *Klebsiella axytoca* (SEQ ID NO: 13), *Klebsiella pneumoniae* (SEQ ID NO: 14), *Providencia stuartii* (SEQ ID NO: 15), and *Serratia marcescens* (SEQ ID NO: 16).

FIG. 3 shows the deduced amino acid sequences of the QRDR for *Escherichia coli* (SEQ ID NO: 36), *Citrobacter freundii* (SEQ ID NO: 37), *Enterobacter aerogenes* (SEQ ID NO: 38), *Enterobacter cloacae* (SEQ ID NO: 39), *Klebsiella oxytoca* (SEQ ID NO: 40), *Klebsiella pneumoniae* (SEQ ID NO: 41), *Providencia stuartii* (SEQ ID NO: 42), and *Serratia marcescens* (SEQ ID NO: 43).

FIGS. 4A and 4B show the alterations in GyrA amino acid sequences and susceptibilities of quinolone resistant clinical isolates of *Escherichia coli, Citobacter freundii, Enterobacter aerogenes, Enterobacter cloacae, Klebsiella oxytoca, Klebsiella pneumoniae, Providencia stuartii*, and *Serratia marcescens*.

DETAILED DESCRIPTION OF THE INVENTION

The present invention provides a simple, rapid and useful method for differentiating Enterobacteriaceae species and determining their quinolone-resistance status. This invention provides materials and methods to apply the species-specific probes to isolated DNA from host samples for an in vitro diagnosis of Enterobacteriaceae infection.

The present invention provides the nucleic acid sequences of conserved and unique regions of the gyrA gene of the following species of the Family Enterobacteriaceae: *Escherichia coli, Citrobacter freundii, Enterobacter aerogenes, Enterobacter cloacae, Kiebsiella oxytoca, Klebsielia pneumoniae, Providencia stuartii* and *Serratia marcescens*. The present invention provides the nucleic acid sequences of the quinolone resistance-determining region (QRDR) and surrounding regions of gyrA of each species listed above.

DNA sequence analyses revealed that gyrA is unique to each species and highly conserved within the species. However, the gyrA mutations resulting in amino acid substitutions which confer quinolone resistance vary in number, type, and position depending on the species. The invention demonstrates that these unique sequences can be used for identification of enteric organisms (genus and species) as well as detection of quinolone resistance within a given species. In addition, comparisons of Enterobacteriaceae gyrA with gyrA sequences from bacteria not closely related to Enterobacteriaceae species suggest that gyrA sequences are unique for all bacterial species and may be used for identification of any species.

The invention provides unique, isolated nucleic acids containing regions of specificity for eight different members of the Family Enterobacteriaceae. These nucleic acids are from the gyrA gene of the Enterobacteriaceae genome. In particular, the invention provides isolated nucleic acids from *Escherichia coli* (SEQ ID NO:1), *Citrobacter freundii* (SEQ ID NO:2), *Enterobacter aerogenes* (SEQ ID NO:3), *Enterobacter cloacae* (SEQ ID NO:4), *Klebsiella oxytoca* (SEQ ID NO:5), *Klebsiella pneumoniae* (SEQ ID NO:6), *Providencia stuartii* (SEQ ID NO:7) and *Serratia marcescens* (SEQ ID NO:8). These sequences can be used to identify and distinguish the respective species of Enterobacteriaceae. FIGS. 1A and 1B show the nucleic acids of SEQ ID NOS:1–8. The sequences correspond to nucleotides #25–613, based on the *E. coli* gyrA sequence numbers of Swanberg et al., *J. Mol. Biol.*, 197:729–736 (1987).

The invention also provides unique, isolated nucleic acids from the quinolone resistance-determining region of *Escherichia coli* (SEQ ID NO:9), *Citrobacter freundii* (SEQ ID NO:10), *Enterobacter aerogenes* (SEQ ID NO:11), *Enterobacter cloacae* (SEQ ID NO:12), *Klebsiella oxytoca* (SEQ ID NO:13), *Klebsiella pneumoniae* (SEQ ID NO:14), *Providencia stuartii* (SEQ ID NO:15) and *Serratia marcescens* (SEQ ID NO:16). These sequences can be used to determine the quinolone resistance status of each species. The QRDR nucleic acids are shown in FIG. 2.

Furthermore, the invention provides specific examples of isolated nucleic acid probes derived from the above, nucleic acid sequences which may be used as species-specific identifiers of *Escherichia coli* (SEQ ID NO:17), *Citrobacter freundii* (SEQ ID NO:18), *Enterobacter aerogenes* (SEQ ID NO:19), *Enterobacter cloacae* (SEQ ID NO:20), *Klebsiella oxytoca* (SEQ ID NO:21), *Klebsiella pneumoniae* (SEQ ID NO:22), *Providencia stuartii* (SEQ ID NO:23) and *Serratia marcescens* (SEQ ID NO:24).

The invention also provides specific examples of isolated nucleic acid probes derived from the QRDR of the above nucleic acid sequences which may be used as determinants of quinolone resistance for *Escherichia coli* (SEQ ID NOS:25 and 26), *Citrobacter freundii* (SEQ ID NO:27), *Enterobacter aerogenes* (SEQ ID NO:28), *Enterobacter cloacae* (SEQ ID NO:29), *Klebsielia oxytoca* (SEQ ID NO:30), *Klebsiella pneumoniae* (SEQ ID NO:31), *Providencia stuartii* (SEQ ID NO:32) and *Serratia marcescens* (SEQ ID NO:33).

Such probes can be used to selectively hybridize with samples containing nucleic acids from species of Enterobacteriaceae. The probes can be incorporated into hybridization assays using polymerase chain reaction, ligase chain reaction, or oligonucleotide arrays on chips or membranes, for example. Additional probes can routinely be derived from the sequences given in SEQ ID NOs:1–8, which are specific for identifying the respective species or for determining quinolone resistance. Therefore, the probes shown in SEQ ID NOs:17–24 and 25–33 are only provided as examples of the species-specific probes or quinolone resistance-determining probes, respectively, that can be derived from SEQ ID NOs:1–8.

By "isolated" is meant nucleic acid free from at least some of the components with which it naturally occurs. By "selective" or "selectively" is meant a sequence that does not hybridiie with other nucleic acids to prevent adequate determination of an Enterobacteriaceae species or quinolone resistance, depending upon the intended result. As used herein to describe nucleic acids, the term "selectively hybridizes" excludes the occasional randomly hybridizing nucleic acids, and thus has the same meaning as "specifically hybridizing".

A hybridizing nucleic acid should have at least 70% complementanty with the segment of the nucleic acid to which it hybridizes. The selectively hybridizing nucleic acids of the invention can have at least 70%, 80%, 85%, 90%, 95%, 97%, 98%, and 99% complementarity with the segment of the sequence to which it hybridizes. The exemplary probes shown in SEQ ID NOs:17–24 and 25–33 are designed to have 100% hybridization with the target DNA.

The invention contemplates sequences, probes and primers which selectively hybridize to the complementary, or opposite, strand of nucleic acid as those specifically provided herein. Specific hybridization with nucleic acid can occur with minor modifications or substitutions in the nucleic acid, so long as functional species-specific or quinolone resistance determining hybridization capability is maintained. By "probe" is meant a nucleic acid sequence that can be used as a probe or primer for selective hybridization with complementary nucleic acid sequences for their detection or amplification, which probe can vary in length from about 5 to 100 nucleotides, or preferably from about 10 to 50 nucleotides, or most preferably about 25 nucleotides. The invention provides isolated nucleic acids that selectively hybridize with the species-specific nucleic acids under stringent conditions. See generally, Maniatis, et al., Molecular cloning: a laboratory manual. Cold Spring Harbor Laboratory, Cold Spring Harbor, N.Y., (1982) latest edition.

Molecular biology techniques permit the rapid detection of hybridization, such as through confocal laser microscopy and high density oligonucleotide arrays and chips. See, Kozal et al., *Nat. Med.*, 2(7): 753–759 (1996), Schummer et al., *Biotech*, 23:1087–1092 (1997) or Lockhart et al., *Nat. Biotech.* 14:1675–1680 (1996). Another example of a detection format is the use of controlled electric fields that permit the rapid determination of single base mismatches, as described in Sosnowski et al., *Proc. Natl. Acad. Sci. USA*, 94:1119–1123 (1997). The invention contemplates the use of the disclosed nucleic acid sequences and probes derived therefrom with these currently available techniques and those new techniques discovered in the future.

If used as primers, the invention provides compositions including at least two oligonucleotides (i.e., nucleic acids) that hybridize with different regions of DNA so as to amplify the desired region between the two primers. Depending on the length of the probe or primer, the target region can range between 70% complementary bases and full complementarity and still hybridize under stringent conditions. For example, for the purpose of diagnosing the presence of the Enterobacteriaceae in a clinical sample, the degree of complementarity between the nucleic acid (probe or primer) and the target sequence to which it hybridizes (e.g., Enterobacteriaceae DNA from a sample) is at least enough to distinguish hybridization with a non-target nucleic acid from other Enterobacteriaceae. The invention provides examples of nucleic acids having sequences unique to Enterobacteriaceae such that the degree of complementarity required to distinguish selectively hybridizing from nonselectively hybridizing nucleic acids under stringent conditions can be clearly determined for each nucleic acid.

Alternatively, the nucleic acid probes can be designed to have homology with nucleotide sequences present in more than one species of Enterobacteriaceae. Such a nucleic acid probe can be used to selectively identify a group of Enterobacteriaceae species. Additionally, the invention provides that the nucleic acids can be used to differentiate Enterobacteriaceae species in general from other species. Such a determination is clinically significant, since therapies for these infections differ.

The invention further provides methods of using the nucleic acids to detect and identify the presence of Enterobacteriaceae, or particular species thereof. The methods involve the steps of obtaining a sample suspected of containing Enterobacteriaceae. The sample, such as blood, urine, lung lavage fluids, spinal fluid, bone marrow aspiration, vaginal mucosa, tissues, etc., may be taken from an individual, or taken from the environment The Enterobacteriaceae cells in the sample can then be lysed, and the DNA released (or made accessible) for hybridization with oligonucleotide probes.

The DNA sample is preferably amplified prior to hybridization using primers derived from the gyrA regions of the Enterobacteriaceae DNA that are designed to amplify several species. Examples of such primers are shown below as GYRA6 (SEQ ID NO:34) and or GYRA631R (SEQ ID NO:35). Detection of and/or the determination of quinolone resistance in the target species of Enterobacteriaceae is achieved by hybridizing the amplified gyrA DNA with an Enterobacteriaceae species-specific probe that selectively hybridizes with the DNA. Detection of hybridization is indicative of the presence of the particular species of Enterobacteriaceae or quinolone resistance, depending upon the probe. In the case where the species of Enterobacteriaceae is known, for example through previous hybridization with a species-specific identifying probe of SEQ ID NOS:17–24, the lack of subsequent hybridization with a species-specific quinolone resistance-determining probe of SEQ ID NOS:25–33 is indicative of quinolone resistance in the sample.

Preferably, detection of nucleic acid hybridization can be facilitated by the use of reporter or detection moieties. For example, the species-specific probes can be labeled with digoxigenin, and a universal-Enterobacteriaceae species probe can be labeled with biotin and used in a streptavidin-coated microtiter plate assay. Other examples of detectable moieties include radioactive labeling, enzyme labeling, and fluorescent labeling.

The invention further contemplates a kit containing one or more species-specific and/or quinolone resistance-determining probes, which can be used for the identification and/or quinolone resistance determination of particular Enterobacteriaceae species. Such a kit can also contain the appropriate reagents for hybridizing the probe to the sample and detecting bound probe. The invention may be further demonstrated by the following non-limiting examples.

EXAMPLES

Example 1

In this Example, the DNA sequence of the gyrA was determined for eight species of Enterobacteriaceae. Oligonucleotide primers were designed from conserved gyrA gene sequences flanking the QRDR and used to amplify and sequence the 5' region of gyrA from ATCC type strains and fluoroquinolone-resistant clinical isolates. The nucleotide and the inferred amino acid sequences were aligned and compared.

The QRDR sequences from 60 clinical isolates with decreased fluoroquinolone susceptibilities were analyzed for alterations associated with fluoroquinolone resistance. The primer sequences at the 3' and 5' ends have been removed leaving nucleotides #25–613, based on the *E. coli* gyrA sequence numbers of Swanberg et al., *J. Mol. Biol.*, 197:729–736 (1987). The organisms, abbreviations and ATCC type strain designation numbers are as follows.

EC=*Escherichia coli* (*E. coli*) ATCC 11775
CF=*Citrobacter freundii* (*C. freundii*) ATCC 8090
EA=*Enterobacter aerogenes* (*E. aerogenes*) ATCC 13048
ECL=*Enterobacter cloacae* (*E. cloacae*) ATCC 13047
KO=*Kiebsiella oxytoca* (*K. oxytoca*) ATCC 13182
KP=*Klebsielia pneumoniae* (*K. pneumoniae*) ATCC 13883
PS=*Providencia stuartii* (*P. stuartii*) ATCC 29914
SM=*Serratia marcescens* (*S. marcescens*) ATCC 13880

Amplification of gyrA
Bacterial Strains and Determination of Antibiotic Susceptibility Profiles.

Type strains of Enterobacteriaceae were from American Type Culture Collection (ATCC). Fluoroquinolone resistant and susceptible clinical isolates, were selected from the Intensive Care Antimicrobial Resistance Epidemiology (ICARE) study, collected from 39 hospitals across the U.S. between June, 1994 and April 1997 (Archibald et al., CID, 24(2):211–215 (1997)). ICARE isolates were screened to exclude duplicate strains from the same patient.

Minimal inhibitory concentrations (MICs) were determined by the broth microdilution method with cation-adjusted Muieller-Hinton broth according to the methods of the National Committee for Clinical Laboratory Standards (NCCLS M7-A4 (1997)). Ciprofloxacin was purchased from Bayer Corporation (West Haven, Conn.), ofloxacin and nalidixic acid were from Sigma (St. Louis, Mo.) and sparfloxacin was from RhOne-Poulenc Rorer (Collegeville, Pa.). Amplification of 5' Region of gyrA.

Oligonucleotide primers were designed based on homologous regions of gyrA sequences in *E. coli* (Swanberg et al., *J. Mol. Biol.*, 1987. 197:729–736) and *K. oxytoca* (published by Dimri et al., *Nuc. Acids Res.*, 1990. 18:(1):151–156 as *K. pneumonia*), as follows:

GYRA6
5'-CGACCTTGCGAGAGAAAT-3' (SEQ ID NO:34)
GYRA631R 5'-GTTCCATCAGCCCTTCAA-3' (SEQ ID NO:35)

Primer GYRA6 corresponds to nucleotides 6 to 23 and primer GYRA631R is complementary to nucleotides 610 to 631 of the *E. coli* gyrA sequence.

DNA fragments were amplified from chromosomal DNA in cell lysates. Amplifications were carried out in a Gene-Amp 9600 PCR System (Perkin-Elmer, Applied Biosystems Division, Foster City, Calif.) in 50 µl volume containing 50 pmol of each primer, 200 µM deoxynucleoside triphosphates, 10 ul cell lysate containing approximately 100 ng template DNA, 1× reaction buffer with 1.5 mM $MgCl^2$ and 1 U native Taq polymerase (Perkin Elmer). An initial 4 minute period of denaturation at 94° C. was followed by 30 cycles including: denaturation for 1 minute at 94° C., annealing for 30 seconds at 55° C., extending for 45 seconds at 72° C., followed by a final cycle of 72° C. for 10 minutes. Amplification products were visualized by agarose gel electrophoresis and ethidium bromide staining to determine specificity and size of gene fragments. PCR products were purified on QIAquick spin columns (QIAGEN, Chatsworth, Calif.) and sequenced with the ABI Prism Dye Terminator or dRhodomine Terminator Cycle Sequencing Kit and an ABI 377 automated sequencer (Perkin Elmer). To eliminate errors due to amplification artifacts, the forward and reverse sequences of each QRDR were determined using products from independent PCR reactions. The GCG (Genetics Computer Group, Madison, Wis.) analyses programs were used for the construction of DNA and amino acid sequence alignments.

The resultant sequences of the gyrA regions for *Escherichia coli, Citrobacter freundii, Enterobacter aerogenes, Enterobacter cloacae, Klebsiella oxytoca, Klebsiella pneumoniae, Providencia stuartii* and *Serratia marcescens* are shown below in Table 1 and in FIGS. 1A–1B. The sequences provided correspond to nucleotide positions 25 to 613 of the gyrA regions for *Escherichia coli*.

TABLE 1

Gyrase A 5' Region Sequences

```
Escherichia coli                                                   (SEQ ID NO:1)
ACACCGGT CAACATTGAG GAAGAGCTGA AGAGCTCCTA TCTGGATTAT
GCGATGTCGG TCATTGTTGG CCGTGCGCTG CCAGATGTCC GAGATGGCCT
GAAGCCGGTA CACCGTCGCG TACTTTACGC CATGAACGTA CTAGGCAATG
ACTGGAACAA AGCCTATAAA AAATCTGCCC GTGTCGTTGG TGACGTAATC
GGTAAATACC ATCCCCATGG TGACTCGGCG GTTTATGACA CGATCGTCCG
TATGGCGCAG CCATTCTCGC TGCGTTACAT GCTGGTAGAC GGTCAGGGTA
ACTTCGGTTC CATCGACGGC GACTCTGCGG CGGCAATGCG TTATACGGAA
ATCCGTCTGG CGAAAATTGC CCATGAACTG ATGGCTGATC TCGAAAAAGA
GACGGTCGAT TTCGTTGATA ACTATGACGG TACGGAAAAA ATTCCGGACG
TCATGCCAAC CAAAATTCCT AACCTGCTGG TGAACGGTTC TTCCGGTATC
GCCGTAGGTA TGGCAACCAA CATCCCGCCG CACAACCTGA CGGAAGTCAT
CAACGGTTGT CTGGCGTATA TCGATGATGA AGACATCAGC A Citrobacter freundii                                               (SEQ ID NO:2)
ACACCGGT CAACATTGAG GAAGAGCTGA AGAGCTCCTA TCTGGATTAT
GCGATGTCGG TCATTGTTGG CCGTGCGCTG CCAGACGTCC GAGATGGCCT
GAAGCCGGTT CACCGTCGCG TACTTTACGC CATGAACGTA TTGGGCAACG
ACTGGAATAA AGCCTATAAA AAATCTGCCC GTGTCGTTGG TGACGTAATC
```

TABLE 1-continued

Gyrase A 5' Region Sequences

```
GGTAAATACC ACCCTCATGG TGATACCGCC GTTTACGACA CCATTGTTCG
TATGGCGCAG CCATTCTCCT TGCGTTACAT GCTGGTAGAT GGTCAGGGTA
ACTTTGGTTC TGTCGATGGC GACTCCGCAG CGGCGATGCG TTATACGGAA
ATCCGTATGT CGAAAATCGC CCATGAGCTG ATGGCTGACC TGGAAAAAGA
AACGGTTGAT TTCGTCGATA ACTACGACGG CACCGAACAA ATTCCTGGAA
TCATGCCGAC CAAAATTCCT AACCTGCTGG TGAACGGTTC GTCCGGTATC
GCGGTAGGTA TGGCGACCAA CATTCCGCCG CACAACCTGA CTGAAGTGAT
CAACGGCTGT CTGGCATATA TTGACGATGA AGACATCAGC A
```

*Enterobacter aerogenes* (SEQ ID NO:3)
```
ACACGGGT CAACATTGAG GAAGAGCTGA AAAGCTCGTA TCTGGATTAT
GCGATGTCGG TCATTGTTGG CCGTGCGCTG CCGGATGTCC GAGATGGCCT
GAAGCCGGTA CACCGTCGCG TACTATACGC CATGAACGTA TTGGGCAATG
ACTGGAACAA AGCCTATAAA AAATCAGCCC GTGTCGTTGG CGACGTAATC
GGTAAATACC ACCCGCATGG TGATACCGCC GTTTATGACA CCATCGTACG
TATGGCGCAG CCGTTCTCCT TGCGTTATAT GCTGGTCGAT GGCCAGGGTA
ACTTTGGTTC TGTCGATGGC GACTCCGCTG CAGCGATGCG TTATACGGAA
ATCCGTATGT CGAAGATCGC TCATGAGCTG ATGGCCGATC TCGAAAAAGA
GACGGTTGAT TTCGTCGACA ACTATGACGG CACGGAGAAA ATCCCTGACG
TCATGCCGAC AAAAATCCCT AACCTGCTGG TGAACGGTTC TTCCGGTATC
GCCGTAGGTA TGGCGACCAA CATTCCGCCG CATAACCTGA CGGAAGTTAT
CAACGGCTGC CTGGCATACG TTGATAACGA AGACATCAGC A
```

*Enterobacter cloacae* (SEQ ID NO:4)
```
ACACCGGTTA ACATCGAGGA AGAGCTGAAG AGCTCCTATC TGGACTATGC
GATGTCGGTC ATTGTTGGCC GTGCGCTGCC GGACGTCCGC GATGGCCTAA
AGCCGGTACA CCGTCGCGTA CTATACGCCA TGAACGTATT GGGCAATGAC
TGGAATAAAG CCTACAAAAA ATCTGCCCGT GTCGTTGGTG ACGTAATCGG
TAAATACCAT CCCCATGGTG ATTCCGCGGT GTACGACACC ATCGTTCGTA
TGGCGCAGCC TTTCTCGCTG CGTTACATGC TGGTAGATGG TCAGGGTAAC
TTTGGTTCTA TCGACGGCGA CTCCGCCGCG GCAATGCGTT ATACGGAAAT
CCGTCTGGCG AAAATTGCCC ATGAGCTGAT GGCCGACCTG GAAAAAGAGA
CGGTTGATTT CGTTGATAAC TACGATGGCA CGGAAAAAAT TCCTGACGTC
ATGCCAACGA AGATCCCTAA CCTGCTGGTG AACGGTTCGT CCGGTATCGC
CGTAGGGATG GCGACCAACA TTCCGCCGCA CAACATCACC GAAGTGATCA
ACGGGTGCCT GGCCTATATC GACGATGAAG ACATCAGCA
```

*Klebsiella oxytoca* (SEQ ID NO:5)
```
ACACCGGT CAACATTGAG GAAGAGCTGA AGAGCTCCTA TCTGGATTAT
GCGATGTCGG TCATTGTTGG CCGTGCGCTG CCGGATGTCC GAGATGGCCT
GAAGCCGGTA CACCGTCGCG TACTATACGC CATGAACGTA TTGGGCAATG
ACTGGAACAA AGCCTATAAA AAATCTGCCC GTGTCGTGGG TGACGTCATC
GGTAAATACC ACCCTCATGG TGATACTGCC GTATACGACA CCATTGTACG
TATGGCGCAG CCATTCTCCC TGCGTTACAT GCTGGTAGAT GGCCAGGGTA
ACTTTGGTTC GGTCGACGGC GACTCCGCCG CAGCGATGCG TTATACGGAA
ATCCGTATGT CGAAGATCGC CCATGAACTG ATGGCCGACC TCGAAAAAGA
GACGGTGGAT TTCGTCGATA ACTATGACGG CACGGAGAAA ATCCCTGACG
TTATGCCGAC CAAAATCCCG AACCTGCTAG TCAACGGTTC GTCCGGTATC
GCGGTAGGTA TGGCGACTAA TATTCCGCCG CACAACCTGA CCGAAGTGAT
CAACGGCTGT CTGGCCTACG TTGAAAACGA AGACATCAGC A
```

*Klebsiella pneumoniae* (SEQ ID NO:6)
```
ACACCGGT CAACATTGAG GAAGAGCTTA AGAACTCTTA TCTGGATTAT
GCGATGTCGG TCATTGTTGG CCGTGCGCTG CCGGATGTCC GAGATGGCCT
GAAGCCGGTA CACCGTCGCG TACTTTACGC CATGAACGTA TTGGGCAATG
ACTGGAACAA AGCCTATAAA AAATCAGCCC GTGTCGTTGG TGACGTAATC
GGTAAATACC ACCCGCACGG CGACTCCGCG GTATACGACA CCATCGTGCG
TATGGCGCAG CCGTTCTCGC TGCGTTACAT GCTGGTGGAC GGCCAGGGTA
ACTTTGGTTC CATCGACGGC GACTCCGCCG CGGCGATGCG TTATACCGAA
ATTCGTCTGG CGAAAATCGC TCATGAGCTG ATGGCCGATC TTGAAAAAGA
GACGGTCGAT TTCGTCGACA ACTATGACGG TACGGAGCGT ATTCCGGACG
TCATGCCGAC CAAAATTCCT AACCTGCTGG TGAACGGCGC CTCCGGGATC
GCCGTAGGGA TGGCCACCAA CATACCGCCA CATAACCTGA CGGAAGTGAT
TAACGGCTGT CTGGCGTATG TTGACGATGA AGACATCAGC A
```

*Providencia stuartii* (SEQ ID NO:7)
```
ACACCGGT CAATATCGAA GAAGAACTCA AAAGTTCGTA TTTGGATTAT
GCGATGTCCG TTATTGTCGG GCGCGCGCTT CCAGATGTTC GAGATGGACT
GAAGCCAGTACACCGCAGAG TACTGTTTGC GATGAATGTA TTGGGAAATG
ATTGGAATAA ACCCTATAAA AAATCTGCCC GTATAGTCGG GGACGTTATC
GGTAAATACC ATCCACATGG TGATAGCGCT GTTTATGAGA CAATCGTTCG
TCTTGCTCAG CCTTTTTCTA TGCGTTATAT GCTGGTAGAT GGTCAGGGGA
ACTTTGGTTC AGTTGACGGA GATTCCGCAG CTGCAATGCG TTATACGGAA
ATCCGTATGG CGAAAATTGC CCATGAAATG TTAGCGGATC TTGAAAAAGA
GACCGTTGAT TTCGTCCCAA ACTATGATGG TACAGAGCAA ATCCCTGAAG
TTATGCCTAC GAAAATCCCT AACCTATTGG TTAATGGTTC GTCAGGTATT
GCTGTTGGGA TGGCAACGAA CATTCCTCCA CACAACCTAG GGGAAGTGAT
```

TABLE 1-continued

Gyrase A 5' Region Sequences

CAGCGGTTGC CTTGCTTATA TAGATGATGA AGATATTAGC A

*Serratia marcescens* (SEQ ID NO:8)
ACACCGGT AAACATCGAA GACGAGTTGA AAAACTCGTA TCTGGACTAT
GCGATGTCCG TTATTGTCGG ACGTGCCCTG CCAGATGTTC GTGATGGACT
GAAGCCGGTT CACCGCCGCG TTCTGTACGC GATGAGCGTA TTGGGTAACG
ACTGGAATAA ACCATACAAG AAATCGGCCC GTGTCGTCGG GGACGTGATC
GGTAAATATC ACCCGCACGG TGACAGCGCG GTTTACGACA CTATCGTGCG
TATGGCTCAG CCGTTTTCAC TGCGCTACAT GCTGGTGGAC GGTCAGGGTA
ACTTCGGTTC CGTCGACGGC GACTCCGCGG CGGCGATGCG TTATACCGAA
GTGCGCATGT CCAAGATTGC TCACGAACTG TTGGCGGATC TGGAAAAAGA
AACCGTCGAC TTCGTGCCTA ACTATGATGG CACCGAGCAG ATCCCGGCCG
TCATGCCGAC CAAGATCCCG AACCTGCTGG TCAACGGCTC GTCGGGCATC
GCCGTGGGCA TGGCTACCAA TATTCCGCCG CACAACCTGG CGGAAGTCGT
CAACGGCTGC CTGGCCTATA TCGACGATGA AAACATCAGC A The QRDR sequences from positions 199 to 318 (relative to *E. coli*) are shown below in Table 2.

TABLE 2

Quinolone Resistance-Determining Region Sequences

*Escherichia coli* (SEQ [001b]ID NO:9)
GCCCG TGTCGTTGGT GACGTAATCG GTAAATACCA TCCCCATGGT
GACTCGGCGG TTTATGACAC GATCGTCCGT ATGGCGCAGC CATTCTCGCT
GCGTTACATG CTGGTAGACG GTCAG

*Citrobacter freundii* (SEQ ID NO:10)
GCCCG TGTCGTTGGT GACGTAATCG GTAAATACCA CCCTCATGGT
GATACCGCCG TTTACGACAC CATTGTTCGT ATGGCGCAGC CATTCTCCTT
GCGTTACATG CTGGTAGATG GTCAG

*Enterobacter aerogenes* (SEQ ID NO:11)
GC CCGTGTCGTT GGCGACGTAA TCGGTAAATA CCACCCGCAT
GGTGATACCG CCGTTTATGA CACCATCGTA CGTATGGCGC AGCCGTTCTC
CTTGCGTTAT ATGCTGGTCG ATGGCCAG

*Enterobacter cloacae* (SEQ ID NO:12)
GC CCGTGTCGTT GGTGACGTAA TCGGTAAATA CCATCCCCAT
GGTGATTCCG CGGTGTACGA CACCATCGTT CGTATGGCGC AGCCTTTCTC
GCTGCGTTAC ATGCTGGTAG ATGGTCAG

*Klebsiella oxytoca* (SEQ ID NO:13)
GCCCGTGTC GTGGGTGACG TCATCGGTAA ATACCACCCT CATGGTGATA
CTGCCGTATA CGACACCATT GTACGTATGG CGCAGCCATT CTCCCTGCGT
TACATGCTGG TAGATGGCCA G

*Klebsiella pneumoniae* (SEQ ID NO:14)
GC CCGTGTCGTT GGTGACGTAA TCGGTAAATA CCACCCGCAC
GGCGACTCCG CGGTATACGA CACCATCGTG CGTATGGCGC AGCCGTTCTC
GCTGCGTTAC ATGCTGGTGG ACGGCCAG

*Providencia stuartii* (SEQ ID NO:15)
GCCCGTATAG TCGGGGACGT TATCGGTAAA TACCATCCAC ATGGTGATAG
CGCTGTTTAT GAGACAATCG TTCGTCTTGC TCAGCCTTTT TCTATGCGTT
ATATGCTGGT AGATGGTCAG

*Serratia marcescens* (SEQ ID NO:16)
GCCCGTGTC GTCGGGGACG TGATCGGTAA ATATCACCCG CACGGTGACA
GCGCGGTTTA CGACACTATC GTGCGTATGG CTCAGCCGTT TTCACTGCGC
TACATGCTGG TGGACGGTCA G Oligonucleotide primers GYRA6 and GYRA631 R successfully amplified the expected 626 bp DNA fragment from *Escherichia coli, Citrobacter freundii, Enterobacter aerogenes, Enterobacter cloacae, Klebsiella oxytoca, Klebsiella pneumoniae, Providencia stuartii* and *Serratia marcescens* (FIGS. 1A–1B). In additional experiments, amplification with GYRA6 and GYRA631 produced the expected GYRA fragment from *S. typhimurium* (data not shown).

The PCR products were sequenced and the 120 bp regions of gyrA known as the QRDR were analyzed. Alignment of the QRDR DNA sequences of the type strains revealed numerous nucleotide substitutions when compared with the *E. coli* sequence (FIG. 2). Eighty-seven of 120 nucleotides (72.5%) were conserved. Similarity to the *E. coli* sequence varied from 93.3% for *E. cloacae* to 80.8% for *P. stuartii*

(FIGS. 4A–4B). Significant diversity was noted when the gyrA QRDR sequen two species from one genus were aligned. *E. aerogenes* and *E. cloacae* shared 90.5% identity and *K. pneumoniae* and *K. oxytoca* shared 89.3 % identity in this region, less similarity than between several of the different genera.

The gyrA QRDR sequence of the *E. coli* type strain (ATCC 11775) was compared with the *E. coli* K12 gyrA sequence published by Swanberg and Wang (*J. Mol. Biol.* 197:729–736 (1997)) and 4 nucleotide differences were detected at positions 255 (C→T), 267 (T→C), 273 (C→T), and 300 (T→C).

When the QRDR sequence from the *K. pneumoniae* type strain was compared with the gyrA gene sequence from *K. pneumoniae* strain M5a1 published by Dimri and Das (*Nucleic Acids Research*, 18:151–156 (1990)), differences were detected in 15 of 120 nucleotides. Of these 15 nucleotides, only one resulted in an amino acid change. At nucleotide position 247 a T to A change altered the deduced amino acid from Ser-83 (ATCC type strain) to Thr (M5a1). When the MSa1 gyrA sequence was compared with that of the *K. oxytoca* type strain, only 4 nucleotide differences were detected. In addition, Ser was consistently found at position 83 in the fluoroquinolone-susceptible strains of *K. pneumoniae* and Thr was consistently found at this position in the *K. oxytoca* strains (FIGS. 4A and 4B). These data indicate that the Dimri and Das-sequence of the M5a1 strain most likely was from a strain of *K. oxytoca* and not *K. pneumoniae*.

In the sequence from the *S. marcescens* type strain (ATCC 13880), the QRDR was identical to the sequence published by Kim et al. (ATCC 14756)(*Antimicrob. Agents Chemother.*, 42:190–193 (1998)). One nucleotide difference was found in the flanking region (nt 321, T to C) with no change in amino acid sequence (data not shown). The *C. freundii* QRDR sequence was identical to that of Nishino et al. (*F E M S Microbiology Letters*, 154:409–414 (1997)), however, an additional 393 nucleotides are presented herein.

The deduced amino acid sequences of the QRDR were highly conserved (FIG. 3). *E. cloacae, K. pneumoniae* and *S. marcescens* shared identical amino acid sequences with *E. coli*. In *C. freundii, E. aerogenes* and *K. oxytoca*, one conservative substitution, Ser-83 to Thr was found. Only *P. stuartii* exhibited more than one amino acid substitution in this region. In this organism two conservative changes were detected, Val-69 to Ile and Asp-87 to Glu. In addition, the Leu-92 and Met-98 positions were reversed when compared with the amino acid sequences of other members of the Enterobacteriaceae family included in this study. The Glu at position 87 is typical for gyrA in Gram-positive organisms (Tankovic et al., *Antimicrob. Agents Chemother.*, 40:2505–2510 (1996)), but has not previously been described for a Gram-negative organism.

After determining the DNA sequence of the QRDR from the quinolone-susceptible type stains the 5' region of gyrA in ciprofloxacin-resistant and -susceptible clinical isolates was amplified, sequenced, and analyzed for mutations leading to amino acid changes associated with fluoroquinolone resistance (FIGS. 4A and 4B). Comparisons of the fluoroquinolone-susceptible type strain and the resistant clinical isolates of *E. coli* revealed single mutations in codon 83 in gyrA associated with low levels of resistance and double mutations (codons 83 and 87) with high levels of resistance ($\geq 16$ ug/ml ciprofloxacin) as previously described (Vila et al., *Antimicrob. Agents Chemother.*, 38:2477–2479 (1994) and Heisig et al., *Antimicrob. Agents Chemother.*, 37:696–701 (1993)). However, in all other species in this study, high levels of resistance were found in strains with single as well as double gyrA mutations. MICs varied significantly among strains with the same mutation, confirming that factors other than gyrA are involved in determining the level of resistance to fluoroquinolones (Everett et al., *Antimicrob. Agents Chemother.*, 40:2380–2386 (1996) and Piddock, *Drugs*, 49 (Suppl) :29–35 (1995)).

All clinical isolates of *C. freundii* with reduced susceptibility to fluoroquinolones were found to have Thr-83 to Ile mutations, resulting from C-to-T substitutions at nucleotide position 248. Two isolates also displayed alterations of Asp-87 to Gly. However, as noted for isolate *C. freundii* 9023 (FIGS. 4A and 4B), the presence of a double mutation was not required for high-level resistance (MICs of 16 μg/ml ciprofloxacin). The nucleotide substitutions in codon 83 of *E. aerogenes* gyrA (Thr-83 to Ile) were identical to those of *C. freundii*. No double mutations were detected in gyrA from 7 strains of *E. aerogenes* with reduced levels of susceptibility to fluoroquinolones. However, MICs of isolates with the single mutation ranged from 2–16 μg/ml ciprofloxacin.

Clinical isolates of *E. cloacae* exhibited numerous substitutions resulting in Ser-83 changes to Phe, Tyr, or Ile with no single amino acid change associated with either low level or high level resistance. There was no alteration of Ser-83 in the clinical isolate *E. cloacae* 1524 which had a marginal decrease in susceptibility to the fluoroquinolones. However, Asp-87 was changed to Asn. This alteration, found as part of a double mutation in *E. cloacae* 1224, may contribute to high-level resistance if additional changes occur in the QRDR of *E. cloacae* 1524.

*K. pneumoniae* isolates exhibited either single or double mutations involving Ser-83 and Asp-87, and ciprofloxacin MICs ranged from 1–16 μg/ml. Again, double mutations were not required for high-level resistance and no specific mutation (Ser-83 to Phe or Tyr) was associated with low or high levels of fluoroquinolone resistance.

*K oxytoca* mutations were confined to the Thr-83 codon and were consistent C-to-T substitutions in the second position resulting in amino acid change to Ile, similar to *C freundii* and *E. aerogenes*. MICs associated with this alteration ranged from 0.5–16 μg/ml ciprofloxacin.

Changes in the QRDR of *P. stuartii* gyrA were also confined to codon 83, however, the nucleotide substitutions varied. The single nucleotide substitutions included A-to-C at the first position or C-to-G at the third position, both resulting in Ser-to-Arg mutations, or G-to-T in the second position resulting in Ser-to-Ile mutations. MICs ranged from 2 to 16 μg/ml ciprofloxacin.

*S. marcescens* displayed the greatest diversity in mutations with Gly-81, Ser-83, or Asp-87 involved. No double mutations were detected in the QRDR of gyrA from 6 fluoroquinolone-resistant clinical isolates. An unusual mutation of Gly-81 to Cys was found in two isolates. However, this mutation has been described in *E. coli* (Yoshida et al., *Antimicrob. Agents Chemother.*, 34:1271–1272 (1990)).

The data in this Example provides for the first time enough comparative nucleic acid sequence data for the gyrA gene to enable one to prepare probes that will selectively hybridize to target nucleic acid to identify the species and/or quinolone resistance of *Escherichia coli, Citrobacter freundii, Enterobacter aerogenes, Enterobacter cloacae, Klebsiella oxytoca, Klebsiella pneumoniae, Providencia stuartii* and *Serratia marcescens*.

Example 2

Development of Probes
Identification of Enterobacteriaceae Species

Oligonucleotide probes can be selected for species-specific identification of Enterobacteriaceae in or near the QRDR of gyrA. The region which includes the codons most often associated with fluoroquinolone resistance (nucleotides 239–263) was not used for the reason that if identification were based on one or more nucleotide changes, the changes associated with resistance would interfere with identification. Each probe for identification was selected for maximum difference, and it is recognized that a smaller region within some probes could be used, based on single base changes. However, most of the probes have at least two nucleotide differences compared with the same region in other strains. When there were variations, other than those associated with resistance, within the susceptible and/or the resistance strains for any given species, the position of the probe was shifted to a region which was completely conserved for all strains sequenced. For this reason, the probes were in the region 5' of the QRDR.

TABLE 3

Oligonucleotide probes for identification of Enterobacteriaceae

E. coli (SEQ ID NO:17)
5' ACT TTA CGC CAT GAA CGT ACT AGG C 3'    (144–168)

C. freundii (SEQ ID NO:18)
5' TGG GCA ACG ACT GGA ATA AAG CC 3'    (164–186)

E. aerogenes (SEQ ID NO:19)
5' TTA TAT GCT GGT CGA TGG CCA G 3'    (297–323)

E. cloacae (SEQ ID NO:20)
5' GCC GGA CGT CCG CGA TGG CCT 3'    (102–122)

K. oxytoca (SEQ ID NO:21)
5' GTA GAT GGC CAG GGT AAC TTT GGT TCG GTC 3'    (307–336)

K. pneumoniae (SEQ ID NO:22)
5' GTG CGT ATG GCG CAG CCG TTC TCG CTG 3' (268–294)

P. stuartii (SEQ ID NO:23)
5' CGT CTT GCT CAG CCT TTT TCT ATG C 3'    (271–295)

S. marcescens (SEQ ID NO:24)
5' GGA ATA AAC CAT ACA AGA AA 3'    (176–195)

Note: Numbers in parentheses refer to base positions in E. coli sequence

Fluoroquinolone Resistance Probes

Simultaneous identification of the species and mutations leading to resistance can be determined by using one of the above oligonucleotide probes in combination with the resistance probes set forth below. All oligonucleotide probes shown in Table 4 for quinolone resistance span the region containing the amino acid codons most frequently associated with resistance (nucleotides 239–263). Susceptible strains will hybridize to the resistance probe for that species and resistance will be detected as one or more basepair mismatch with the susceptible strain sequence.

TABLE 4

Oligonucleotide probes for quinolone resistance in Enterobacteriaceae

E. coli (SEQ ID NO:25)
5' ATG GTG ACT CGG CGG TTT ATG ACA C 3'
OR (SEQ ID NO:26)
5' ATG GTG ACT CGG CGG TCT ATG ACA C 3'

C. freundii (SEQ ID NO:27)
5' ATG GTG ATA CCG CCG TTT ACG ACA C 3'

E. aerogenes (SEQ ID NO:28)
5' ATG GTG ATA CCG CCG TTT ATG ACA C 3'

E. cloacae (SEQ ID NO:29)
5' ATG GTG ATT CCG CGG TGT ACG ACA C 3'

K. oxytoca (SEQ ID NO:30)
5' ATG GTG ATA CTG CCG TAT ACG ACA C 3'

K. pneumoniae (SEQ ID NO:31)
5' ACG GCG ACT CCG CGG TAT ACG ACA C 3'

P. stuartii (SEQ ID NO:32)
5' ATG GTG ATA GCG CTG TTT ATG AGA C 3'

S. marcescens (SEQ ID NO:33)
5' ACG GTG ACA GCG CGG TTT ACG ACA C 3'

---

What is claimed is:

1. An isolated nucleic acid probe of 20–50 nucleotides in length for identifing an Enterobacteriaceae species in a sample, wherein the probe is at least 90% homologous to the 5' region of the gyraseA gene of *Escherichia coli* (SEQ ID NO: 1), or a fully complementary sequence thereof, but is not at least 90% homologous to the 5' region of the gyraseA gene of *Citrobacter freundii* (SEQ ID NO: 2), *Enterobacter aerogenes* (SEQ ID NO: 3), *Enterobacter cloacae* (SEQ ID NO: 4), *Klebsiella oxytoca* (SEQ ID NO: 5), *Klebsiella pneumoniae* (SEQ ID NO: 6), *Providencia stuartii* (SEQ ID NO: 7), or *Serratia marcescens* (SEQ ID NO: 8).

2. The isolated nucleic acid probe of claim 1, wherein the probe comprises a nuclotide sequence having a sequence as set forth as SEQ ID NO: 17, or a fully complementary sequence thereof.

3. The probe of claim 1, wherein the probe comprises 25 consecutive nucleotides of SEQ ID NO: 1.

4. The isolated nucleic acid probe of claim 1, wherein the probe is at least 95% homologous to the 5' region of the gyraseA gene of *Escherichia coli* (SEQ ID NO: 1), or a fully complementary sequence thereof, but not at least 95% homologous to the 5' region of the gyraseA gene of *Citrobacter freundii* (SEQ ID NO: 2), *Enterobacter aerogenes* (SEQ ID NO: 3), *Enterobacter cloacae* (SEQ ID NO: 4), *Klebsiella oxytoca* (SEQ ID NO: 5), *Klebsiella pneumoniae* (SEQ ID NO: 6), *Providencia stuartii* (SEQ ID NO: 7), or *Serratia marcescens* (SEQ ID NO: 8).

5. The isolated nucleic acid probe of claim 1, wherein the probe is at least 97% homologous to the 5' region of the gyraseA gene of *Escherichia coli* (SEQ ID NO: 1), or a fully complementary sequence thereof, but is not at least 97% homologous to the 5' region of the gyraseA gene of *Citrobacter freundii* (SEQ ID NO: 2), *Enterobacter aerogenes* (SEQ ID NO: 3), *Enterobacter cloacae* (SEQ ID NO: 4), *Klebsiella oxytoca* (SEQ ID NO: 5, *Klebsiella pneumoniae* (SEQ ID NO: 6), *Providencia stuartii* (SEQ ID NO: 7), or *Serratia marcescens* (SEQ ID NO: 8).

6. The isolated nucleic acid probe of claim 1, wherein the probe is at least 98% homologous to the 5' region of the gyraseA gene of *Eschericha coli* (SEQ ID NO: 1), or a fully complementary sequence thereof, but is not at least 98% homologous to the 5' region of the gyraseA gene of *Citrobacter freundii* (SEQ ID NO: 2), *Enterobacter aerogenes* (SEQ ID NO: 3), *Enterobacter cloacae* (SEQ ID NO: 4), *Klebsiella oxytoca* (SEQ ID NO: 5), *Klebsiella pneumoniae* (SEQ ID NO: 6), *Providencia stuartii* (SEQ ID NO. 7), or *Serratia marcescens* (SEQ ID NO: 8).

7. The isolated nucleic acid probe of claim 1, wherein the probe is at least 99% homologous to the 5' region of the gyraseA gene of *Escierichia coli* (SEQ ID NO: 1), or a fully complementary sequence therof, but is not at least 99% homologous to the 5' region of the gyrasA gene of *Citrobacter freundii* (SEQ ID NO: 2), *Enterobacter aerogenes* (SEQ ID NO: 3), *Enterobacter cloacae* (SEQ ID NO: 4) *Klebsiella oxytoca* (SEQ ID NO: 5), *Klebsiella pneumoniae* (SEQ ID NO: 6), *Providencia stuartii* (SEQ ID NO: 7), or *Serratia marcescens* (SEQ ID NO: 8).

8. The isolated nuleic acid probe of claim 1, wherein the probe is 100% homologous to the 5' region of the gyraseA gene of *Escherichia coli* (SEQ ID NO: 1), or a fully complementary sequence thereof, and is not 100% homologous to the 5' region of the gyraseA gene of *Citrobacter freundii* (SEQ ID NO: 2), *Enterobacter oxytoca* (SEQ ID NO: 3), *Enterobacter cloacae* (SEQ ID NO: 4), *Klebsiella oxytoca* (SEQ ID NO, 5), *Klebsiella pneumoniae* (SEQ ID NO: 6), *Providencia stuartii* (SEQ ID NO: 7), or *Serratia marcescens* (SEQ ID NO: 8).

9. The isolated nucleic acid probe of claim 1, wherein the probe is 25 to 50 nucleotides in length.

10. A method of identifying in a sample an *Escherichia coli*, comprising combining the sample with a nucleic acid probe of 20–50 nucleotides in length, wherein the probe hybridizes to the 5' region of the gyraseA gene of *Escherichia coli* (SEQ ID NO: 1), or a fully complementary sequence thereof, but does not hybridize to a nucleic acid having a sequence as set forth as SEQ ID NOs: 2–8, wherein the presence of hybridization with a nucleic acid idenfifies the *Escherichia coli* in the sample.

11. The method of claim 10, wherein probe comprises the nucleotide sequence as set forth as SEQ ID NO: 17.

12. The method of claim 10, wherein the probe is 25 to 50 nucleotides in length.

13. An isolated nucleic acid probe of 20–50 nucleotides in length capable of determining quinolone resistance status of an *Escherichia coli* in a sample, wherein the probe hybridizes to the 5' region of the gyraseA gene of *Escherichia coli* (SEQ ID NO: 1), or a fully complementary sequence thereof, and wherein a nucleic acid a quinolone susceptible strain of *Escherichia coli* hybridizes to the probe, and wherein a nucleic acid a quinolone resistant strain of *Eschenchia coli* has a one or more base pair mismatch with the probe.

14. The isolated nucleic acid probe of claim 13, wherein the probe comprises a nucleolide sequence having a sequence as set forth as SEQ ID NO: 25 or SEQ ID NO: 26, or a fully complementary sequence therof.

15. The probe of claim 13, wherein the probe comprises 25 conseutive nucleotides of SEQ ID NO: 1.

\* \* \* \* \*

UNITED STATES PATENT AND TRADEMARK OFFICE
CERTIFICATE OF CORRECTION

PATENT NO. : 6,706,475 B1  
DATED : March 16, 2004  
INVENTOR(S) : Weigel et al.

Page 1 of 1

It is certified that error appears in the above-identified patent and that said Letters Patent is hereby corrected as shown below:

Title page,  
Insert Item -- Related U.S. Application Data  
[60]    Provisional application No. 60/080,375, April 1, 1998. --

Column 1,  
Line 10, please insert the following:
-- PRIORITY CLAIM  
       This is the § 371 U.S. national phase of PCT Application No. PCT/US99/06963, filed March 30, 1999, which claims the benefit of U.S. Provisional Patent Application No. 60/080,375, filed April 1, 1998. --

Signed and Sealed this

Twenty-first Day of December, 2004

JON W. DUDAS  
*Director of the United States Patent and Trademark Office*

UNITED STATES PATENT AND TRADEMARK OFFICE
CERTIFICATE OF CORRECTION

PATENT NO. : 6,706,475 B1
DATED : March 16, 2004
INVENTOR(S) : Weigel et al.

It is certified that error appears in the above-identified patent and that said Letters Patent is hereby corrected as shown below:

Column 5,
Line 7, "…not hybridiie with other nucleic acids…" should read -- not hybridize with other nucleic acids… --.

Column 6,
Line 23, "…or taken from the environment The Enterobacteriaceae…" should read -- …or taken from the environment. The Enterobacteriaceae… --.

Column 7,
Line 45, "…RhOne-Poulenc Rorer…" should read -- …Rhône-Poulenc Rorer… --.

Column 8,
Line 22, "$MgCl^2$" should read -- $MgCl_2$ --.

Column 11,
Table 2, "(SEQ [001b]ID NO:9)" should read -- (SEQ ID NO:9) --.

Column 13,
Line 2, "…gyrA ARDR sequen two species…" should read -- …gyrA ARDR sequences of two species… --.
Line 21, "When the MSa1 gyrA sequence…" should read -- When the M5a1 gyrA sequence… --.
Line 54, "…the quinolone-susceptible type stains the 5' region…" should read -- …the quinolone-susceptible type strains, the 5' region… --.

UNITED STATES PATENT AND TRADEMARK OFFICE
CERTIFICATE OF CORRECTION

PATENT NO.    : 6,706,475 B1
DATED         : March 16, 2004
INVENTOR(S)   : Weigel et al.

It is certified that error appears in the above-identified patent and that said Letters Patent is hereby corrected as shown below:

Column 31,
Line 1, "...and wherein a nucleic acid a quinolone..." should read -- ...and wherein a nucleic acid from a quinolone... --.
Line 3, "...wherein a nucleic acid a quinolone..." should read -- ...wherein a nucleic acid from a quinolone... --.

Signed and Sealed this

Twenty-eighth Day of February, 2006

JON W. DUDAS
*Director of the United States Patent and Trademark Office*